United States Patent

Maurer

[11] Patent Number: 5,876,206
[45] Date of Patent: Mar. 2, 1999

[54] METHOD FOR DRIVING A TOOTH-CLEANING ELEMENT

[76] Inventor: Andreas Maurer, Blumenfeldstrasse 55, 8046, Zürich, Switzerland

[21] Appl. No.: 351,418
[22] PCT Filed: Apr. 5, 1994
[86] PCT No.: PCT/CH94/00068
    § 371 Date: Feb. 15, 1995
    § 102(e) Date: Feb. 15, 1995
[87] PCT Pub. No.: WO94/23667
    PCT Pub. Date: Oct. 27, 1994

[30] Foreign Application Priority Data

Apr. 15, 1993 [CH] Switzerland ............ 01 140/93

[51] Int. Cl.[6] ............................................. A61C 15/00
[52] U.S. Cl. ........................... 433/216; 433/118; 15/22.1; 15/2.2
[58] Field of Search .................. 433/118, 119, 433/216; 601/142, 139; 132/322; 15/22.1, 22.2, 22.4, 28

[56] References Cited

U.S. PATENT DOCUMENTS

| | | | |
|---|---|---|---|
| 1,792,358 | 2/1931 | Byers et al. | 15/22.2 |
| 2,567,798 | 9/1951 | Bamberger | 15/22.2 |
| 3,978,852 | 9/1976 | Annoni | 433/118 |
| 4,223,417 | 9/1980 | Solow | 15/22.1 |
| 4,795,347 | 1/1989 | Maurer | 15/22.1 |
| 5,177,826 | 1/1993 | Vrignaud et al. | 15/28 |

FOREIGN PATENT DOCUMENTS

| | | | |
|---|---|---|---|
| 2715414 | 10/1978 | Germany | A46B 13/00 |
| 8911427 | 11/1989 | Germany | A46B 9/04 |

*Primary Examiner*—Nicholas D. Lucchesi
*Attorney, Agent, or Firm*—Antonelli, Terry, Stout & Kraus, LLP

[57] ABSTRACT

A method and device for enabling oscillating drive of at least one tooth cleaning element in a tooth cleaning device which includes a drive unit and motion transmitters acting between the drive unit and the at least one tooth cleaning element. A rotary motion, derived from the rotary motion of the drive unit, is converted and one of the motion transmitters in a vicinity of at least one tooth cleaning element into a cyclic linear motion directed at an angle to an axis of the rotary motion of the drive unit and transmitted to the cleaning element.

18 Claims, 14 Drawing Sheets

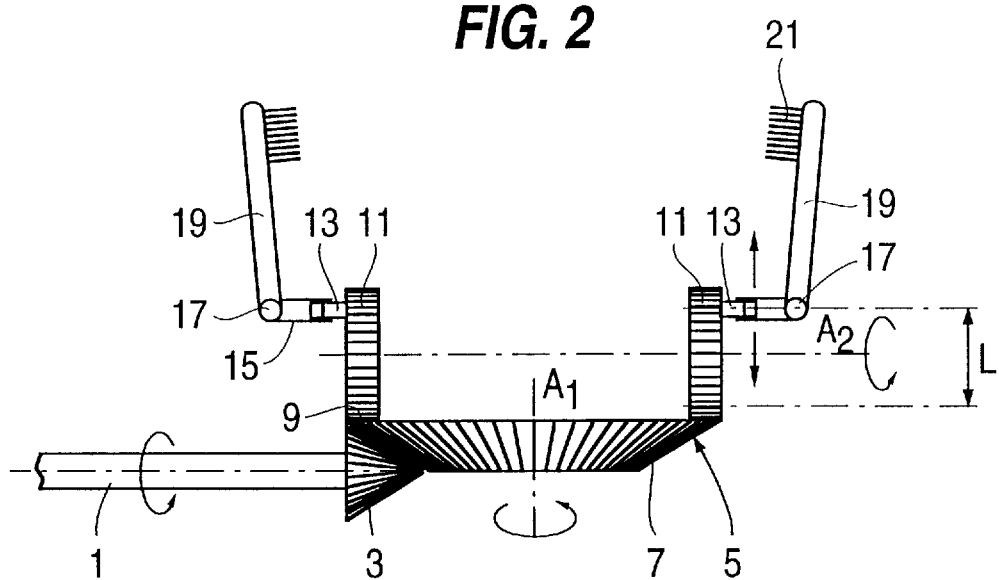
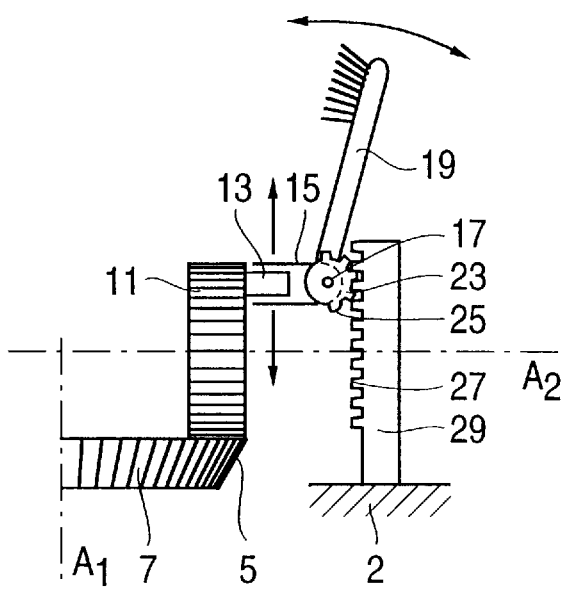

METHOD FOR DRIVING A TOOTH-CLEANING ELEMENT

FIELD OF THE INVENTION

The present invention relates to a method for oscillating drive of at least one tooth-cleaning element on an electric toothbrush with a drive unit and a motion transmitter acting between the drive unit and the at least one tooth cleaning elements and a brush head suitable for working the method.

BACKGROUND OF THE INVENTION

In, for example, DE-27 15 414 and U.S. Pat. No. 3,978, 852, electric toothbrush arrangements are provided wherein a toothbrush includes a drive shaft driven in a drive unit, for example, a handle housing. The rotary motion of the drive shaft is converted to a cyclic linear motion in the housing itself in order to move a toothbrush head mounted in the handle housing back and forth as a unit.

In German Utility Model DE-G 89 11 427.2 an electric toothbrush is proposed in which a drive shaft projects through the head of the brush and moves a toothbrush mounted endwise back and forth with a cyclic linear motion derived from the shaft. The rotary axis of the cyclic linear motion runs parallel to the rotational axis of the drive shaft.

An electric toothbrush according to European Patent Application No. 0 173 114, with the present patent application being a continuation and improvement on said European patent application.

As in the above-mentioned European patent application, it is important that the various tooth surfaces be cleaned equally well by a cleaning device. Therefore it is important that, in particular the inner, that is, facing the oral cavity, as well as the gums, and the outer tooth surfaces, that is the tooth surfaces facing the cheeks of the user, and the gums themselves, all be cleaned equally, as well as possible. It is also important that the best possible local cleaning pressure be provided at all points to be cleaned. Finally, it is important that the cleaning elements perform optimum movements, that is, movement directed from the gum outward and toward the crown of the tooth as coaxially as possible with respect to the tooth, and not in the opposite direction.

In the above-mentioned European Patent Application No. 0 173 114, which is an integral component of the present application, the method for cleaning the teeth by an electric toothbrush is especially important for the present application, which states that it is important that cleaning be performed simultaneously on at least two sides of the tooth. The method defined according to European Patent Application No. 0 173 114 and important to the invention as well as the device features of the electric toothbrush thus defined, in combination with the features of the invention defined below for the present invention, constitute features of the present patent application that are essential to the invention.

In EP-A-0 173 114, the various motions in a electric toothbrush defined according to the invention are executed primarily with pneumatically or hydraulically operable drive elements. Although the hydraulically or pneumatically operable drive elements have proven themselves, one goal of the present invention is to refine the drive mechanism further and to simplify it in order firstly to increase further the operational safety of electric toothbrushes, to reduce manufacturing costs, and finally to permit a smaller design for the cleaning heads.

SUMMARY OF THE INVENTION

The aim underlying the present invention essentially resides in providing a method and device for oscillating a drive of at least one tooth cleaning element in a tooth cleaning device, with the oscillating device comprising a drive unit and motion transmitters acting between the drive unit and the cleaning element. The method comprises the steps of deriving a motion from the rotary motion of the drive and converting the rotary motion into a motion transmitter in a vicinity of at least one tooth cleaning element into a cyclic linear motion directed at an angle to an axis of the rotary motion of the drive unit and transmitting the cyclic linear motion to the at least one cleaning element.

According to the present invention a method is proposed for oscillating drive of at least one tooth-cleaning element on an electric toothbrush with a drive unit as well as motion transmitters operating between the drive unit and the cleaning element, whereby at least one rotary motion derived from a rotary motion of the drive unit is converted into a cyclic linear motion in the motion transmitter, with the motion being at right angles to the axis of the rotary motion of the drive unit, and with the said cyclic linear motion being transmitted to the cleaning element.

According to one embodiment of the method of the present invention, the cyclic linear motion is superimposed in the motion transmitter on a rotary motion essentially perpendicular to the direction of the cyclic linear motion, whereby the cyclic linear motion is transmittable to the cleaning element and the cleaning element is simultaneously rotatable around the motion transmitter.

According to one variation on the method, the rotary motion of the drive unit on the motion transmitter is converted into a rotary motion around a second rotational axis, with the axis being directed essentially parallel to or at an oblique angle to the axis of the drive unit, and with the second rotary motion being converted into a cyclic linear motion essentially parallel to the plane of the rotary motion around the second axis, and being transmitted to the cleaning element.

According to another embodiment of the method for oscillating drive, it being proposed that a rotary motion derived at least from a rotary motion of the drive unit around a first axis be converted into a rotary motion around a second axis, with the axis being at an angle to the first, with the rotary motion around the second axis being converted into a cyclic linear motion essentially parallel to the plane of the rotary motion around the second axis and transmitted to the cleaning element.

By the cyclic linear motion, generated according to one of the methods described above for example a reciprocating motion of the cleaning element relative to the electric toothbrush or relative to the teeth to be cleaned can be effected.

According to another embodiment of the method according to the invention, it is also possible, by the cyclic linear motion, to effect at least two relative motions of the cleaning element relative to the electric toothbrush or the teeth to be cleaned, as for example the abovementioned reciprocating motion and a pivoting motion of the tooth-cleaning element around a pivot axis on the element.

A method is also proposed for cyclic linear drive of at least one cleaning element, on which cleaning element a cyclic linear reciprocating motion is effected by means of a drive unit, with the linear reciprocating motion acting transversely on one pivot axis of the cleaning element to effect the reciprocating motion of the cleaning element or elements, and rotational means disposed on the pivot axis are simultaneously set rotating in one direction with a downward stroke or in the other direction with an upward stroke, by means of which rotational means or by whose rotation the cleaning element or elements is/are given a cyclic linear pivoting motion.

The rotational means are preferably set rotating by rolling along a plane, preferably parallel to the cyclic linear motion, and the rotational motion is preferably transmitted to the cleaning element or elements to effect the cyclic linear motion by friction.

Preferably, the cyclic linear motion generated in the motion transmitter by one of the abovementioned methods according to the invention and transmitted to the cleaning element, simultaneously effects the cyclic linear and/or reciprocating motion of the pivot axis, whereby the cleaning element or elements are simultaneously given a cyclic linear motion by rotation of the rotational means.

According to another method according to the invention for oscillating pivoting drive of at least one cleaning element, on which cleaning element a cyclic linear reciprocating motion is effected by a drive unit, it is proposed that tensioning or click-spring means be provided with the, means being effectively linked with the cleaning element or elements and positioning the latter in two pivot positions with pretensioning, with tensioning or click-spring means being tensioned or relaxed or retensioned by a motion system during the reciprocating motion and with the cleaning element or elements or their pivot axes being pivoted between the two positions.

It is also possible for the cyclic linear reciprocating motion to be effected for tensioning or relaxing or retensioning the tension or click-spring type means by the cyclic linear motion produced in the motion transmitter by the rotary motion derived from the drive unit and converted therein.

According to yet another method according to the invention for oscillating pivoting drive of at least one cleaning element, on which cleaning element a cyclic linear reciprocating motion is effected by means of a drive unit, it is proposed that by another cyclic linear reciprocating motion, a pivot element linked leverwise with the cleaning element is actuated in synchronization with the cyclic linear reciprocating motion against a spring force in such manner that during one reciprocating motion of the cleaning element the latter is driven into one pivot position by the pivot element, and during the other reciprocating motion it is driven by the spring force into the other pivot position.

It is also advantageous in this regard that the rotary motion derived by means of the motion transmitter from the drive unit is converted into two cyclic linear motions, with one cyclic linear motion producing the stroke and the other cyclic linear motion acting on the pivoting element to effect the cyclic linear motions of the cleaning element.

Preferably, the rotary motion is converted in the motion transmitter into two cyclic linear motions with different lengths of travel, with the one cyclic linear motion being transmitted transversely to a pivot axis on the cleaning element in order to effect a reciprocating motion of the tooth-cleaning element relative to the cleaning device or relative to the teeth to be cleaned, and the other oscillating motion acting as a pivot drive on the pivot element in order to effect the cyclic linear motion of the cleaning element.

A tooth-cleaning device suitable for working the method defined according to the invention is proposed with a drive unit for effecting tooth cleaning of cleaning elements driven with oscillation by the drive unit, with the drive unit having at least one undulating element and with at least one rotary motion transmitter being effectively connected therewith, suitable for creating at least one cyclic linear motion, said motion transmitter being effectively linked with the cleaning elements in order to produce a reciprocating motion of at least a portion of the cleaning elements.

The tooth-cleaning device proposed according to the invention comprises a handle and a head part, with the tooth-cleaning elements being provided on or in a cleaning head provided essentially at least nearly endwise on the head part, and with at least two sets of cleaning elements being disposed on the cleaning head opposite one another and acting in opposite directions, in order to perform at least a cyclic reciprocating motion relative to the cleaning head and a cyclic linear motion relative to the other set of cleaning elements.

According to one embodiment of the tooth-cleaning device, the undulating drive unit extends from the handle through the head part to the cleaning head mounted endwise, with the drive unit being connected by a worm, bevel, or angular gear of a corresponding worm, bevel, or angle drive with at least one first motion transmitting element disposed in the cleaning head and driving the latter, the element preferably being a rotational element, for example a gear, disk, or cylindrical element, with at least one shaft, pin, or cam-type element disposed eccentrically with respect to its rotational axis. The motion transmitting element and the eccentric element are arranged so that a cyclic linear motion is produced at an angle relative to the rotational axis of the drive shaft.

According to one embodiment of the tooth-cleaning device it is proposed that the first motion transmitting element be formed by at least two gear, disk, or cylindrical elements located opposite one another, each comprising on its exterior at least one eccentric element, with the eccentric element being connected to rotate freely around the motion transmitting element and displaceably in the oscillation direction, and with the element being effectively linked with at least a portion of the cleaning elements in order to effect the reciprocating motion thereon. By means of this support element, freely rotatable around the motion transmitting element, it is possible that in the case of a cleaning head made in two parts, for one part of the head, comprising at least a portion of the cleaning elements, to be linked movably with the other part, for example, a base part of the cleaning head, with the cyclic linear motion being transmittable to the cleaning elements in nearly every position assumed relative to the base part for effecting the reciprocating motion.

The design of the motion transmitting element or elements as well as the cyclic linear elements, eccentric elements, and any transmitting elements intended to transfer cyclic linear motion to the cleaning elements, is diverse, and possible embodiments will be explained below in greater detail with reference to the attached figures.

For effecting oscillating cyclic linear motion of the cleaning elements, as proposed according to the method defined above, additional embodiments of an electric toothbrush are proposed in which at least a portion of the tooth-cleaning elements, for example brush heads, are mounted rotatably and pivotably movably around a pivot axis. As a rule, the cyclic linear motion of the cleaning elements is effected between two positions, namely one position remote from and pivoted away from the teeth, and one abutting the teeth and tilted forward, in which position the cleaning of the teeth is performed.

To execute this cyclic linear motion of the tooth-cleaning elements, for example brush heads, various designs are proposed according to the invention, that can be operated both as a function of the cyclic linear motion described above or can also be operated by drive assemblies independent thereof.

According to one embodiment, it is proposed to provide roller, cylinder, or gear-type rotational elements on the pivot axes of the tooth-cleaning elements, with the elements being effectively linked by friction for example with the tooth-cleaning elements or with the pivot axis, with and with the roller, gear, or cylindrical rotational elements resting against a complementary wall or plane or engaging therewith during the execution of a cyclic linear or reciprocating motion of the pivot axis, said motion being performed perpendicularly to the axis, and being rotated around this pivot axis, whereby a cyclic linear motion of the tooth-cleaning elements is effected by friction. In this way it is possible for the cyclic linear or reciprocating motion of the pivot axis responsible for the cyclic linear motion of the cleaning elements to be produced by means of a drive unit independently of the motion transmission element or for this cyclic linear motion to be identical with the cyclic linear motion generated by the motion transmitting element.

The rotational elements can be effectively linked by friction either with the pivot axis and/or with at least a portion of the cleaning elements, in such manner that the cleaning elements are driven into one pivot position during rotation in one direction and are driven into the other pivot position during rotation in the other direction.

According to another embodiment of the tooth-cleaning device, tensioning or click-spring means are provided, with the means being effectively connected with at least a portion of the cleaning elements and causing them to be brought into two pivoting positions, with the cleaning elements opposite one another and acting in opposite directions each being arranged to pivot around a pivot axis from one pivot position into the other, and vice versa. In addition, at least one reference system is provided to tension the tensioning or click-spring means by moving the pivot axis by a reciprocating motion toward and/or away from the reference systems or to relax or retension the click-spring means, with the tooth-cleaning elements being arranged in one pivot position or the other, pivoted inward or outward relative to the cleaning head or the teeth to be cleaned.

It is also possible for the reciprocating motion of the pivot axis to be effected by an independent drive element or by means of the cyclic linear motion generated by the motion transmitting element.

According to yet another tooth-cleaning device according to the invention, a drive element is provided to generate an additional cyclic linear motion, as well as a pivot element connected leverwise with at least a portion of the cleaning elements, with the element being operable by means of the additional cyclic linear motion in order to hold the cleaning elements in one pivot position. In addition, spring means are provided by which the cleaning elements are drivable with pretensioning into another pivot position opposite a pivot position. By means of the latter, the cleaning elements are driven into the other pivot position when the pivot element connected leverwise with the cleaning elements is not actuated.

In turn, it is possible for an independently acting drive element to be provided or for the drive element to be identical with the drive unit and for the motion element to be effectively linked with at least two eccentric elements to generate both cyclic linear motions.

In order to permit individual adjustment of the tooth-cleaning elements in the tooth-cleaning device characterized most recently to the teeth to be cleaned, it is advantageous for the cleaning elements to have at least one rubber-mounted or rubber-elastic segment in order for it to adapt optimally to varying contours.

According to the present invention, the cyclic linear motion and the motion transmitter is superimposed on a rotary motion preferably perpendicular to a direction of the cyclic linear motion whereby the cyclic linear motion is transmittable to the at least one cleaning element and the cleaning element is simultaneously rotatable around the motion transmitter.

Advantageously, the rotary motion of the drive unit is converted into a rotary motion around a second axis which extends mainly parallel or slightly at an angle to the axis of the rotary motion of the drive unit, with the rotary motion being converted into a cyclic linear motion essentially parallel to a plane of rotary motion around a second axis and being transmitted to the at least one cleaning element.

The rotary motion around the first axis, derived from the rotary motion of the drive unit, is converted into a rotary motion around the second axis and an angle to the first axis, with the rotary motion around the second axis being converted into a cyclic linear motion essentially parallel to a plane of rotary motion around the second axis and transmitted to the cleaning element.

According to the present invention, by means of the cyclic linear motion, a reciprocating motion of the at least one tooth cleaning element is performed relative to one of the cleaning device or relative to the teeth to be cleaned by cyclic linear motion.

At least two relative motions of the cleaning element relative to at least one of the cleaning device or the teeth to be cleaned are effected by means of the cyclic linear motion, especially a reciprocating motion and a pivoting motion around a pivot axis on the at least one tooth cleaning element.

In accordance with the method of the present invention for the oscillating drive of at least one cleaning element, with the oscillating drive including a drive unit for effecting a cyclic linear reciprocating motion on the at least one cleaning element, the method includes the steps of effecting the cyclic linear motion so as to act transversely on a pivot axis of the at least one cleaning element to effect a reciprocating motion of the at least one cleaning element, with rotation means being mounted on the pivot axis of the at least one cleaning element simultaneously rotating the at least one cleaning element during the cyclic linear motion with the at least one cleaning element rotating in one direction during an upward stroke and in the other direction during a downward stroke by which the rotary motion of the rotary means imparts the cyclic linear motion to the at least one cleaning element. The rotary means are set into rotation by rolling along a plane or planar member cooperable with the rotary means preferably parallel to the cyclic linear motion, and the rotary motion is transmitted to the at least one cleaning element to produce cyclic linear motion by friction.

Advantageously, the cyclic linear motion produced in the motion transmitter and transmitted to the at least one cleaning element simultaneously produces at least one of a cyclic linear or reciprocating motion of the pivot axis of the at least one cleaning element and simultaneously through rotation of the rotary unit causes the at least one cleaning element to perform a cyclic linear motion.

In accordance with the present invention, a tensioning or click-spring type means is provided, with the means having an operating connection with the at least one cleaning element and being adapted to position the latter with a pretensioning in two pivot positions. The tensioning or click-spring type means selectively tensions, relaxes, and re-tensions the at least one cleaning element by at least one reference system during the cyclic linear reciprocating motion so that the at least one cleaning element or a pivot axis of the at least one cleaning element is pivoted back and forth between the two pivot positions.

The cyclic linear motion is produced in a motion transmitter and is transmitted to the at least one cleaning element and simultaneously causes cyclic linear and reciprocating motion of the pivot axis of the at least one cleaning element and simultaneously causes the cleaning element to perform a cyclic linear motion by tensioning, relaxing and re-tensioning by the tensioning means.

In accordance with the method of the present invention, a pivot element is connected through levers with the at least one cleaning element. The cleaning element is actuated synchronously with the pivot element with the cyclic linear reciprocating motion against a spring force by another cyclic linear motion with the pivot element being driven by the another cyclic linear motion in such a manner that during one stroke of the cleaning element at least one cleaning element is driven into a first pivot position by the pivot element and is driven by the spring force into a second pivot position.

The rotary motion in the method of the present invention is derived from a drive unit through the motion transmitter with the rotary motion being converted into two cyclic linear motions, with one cyclic linear motion producing a stroke of the at least one cleaning element and the other cyclic linear motion acting on the pivot element to produce the cyclic linear motion of the cleaning element.

Advantageously, the rotary motion is effected around the second axis and is converted into two cyclic linear motions with different strokes, with the cleaning element being pivotably mounted and, in one cyclic linear motion being transmitted transversely to the pivot axis with the other cyclic linear motion acting as a pivot drive on the pivot axis.

In accordance with the present invention, a tooth cleaning device is provided for reinforcing tooth cleaning by cleaning elements driven in an oscillating manner with the tooth cleaning device including a drive unit having at least one undulating element and at least one rotating motion transmitter effectively linked therewith for producing at least a cyclic linear motion, the motion transmitter is effectively linked with the cleaning elements to produce a reciprocating motion in at least a portion of the cleaning elements. According to further features of the present invention, the tooth cleaning device includes a handle and a head part provided in addition to the cleaning elements, with the cleaning elements being mounted at or in a cleaning head located mainly endwise on the head part. At least two portions of the cleaning elements on the cleaning head are mounted opposite one another and act against one another in order to produce at least one reciprocating motion relative to the cleaning head and a cyclic linear motion relative to the other portion of the cleaning elements.

In the tooth cleaning device of the present invention, the at least two portions of the cleaning elements of the cleaning head, as viewed from a tooth, are disposed so as to surround the tooth in a concave manner such that the cleaning elements surround the teeth on at least two sides thereof.

The cleaning head is advantageously composed of at least two parts with the two parts being movable connected with each other and with one of the parts forming a base part.

The drive units of the two cleaning devices of the present invention includes a drive shaft connected by an endwise worm, bevel or ankle gear with at least one first motion transmitter element located in a cleaning head and driving the cleaning head. The at least one first motion transmitting element is preferably wheel-shaped, disc-shaped or fashioned as a cylindrical element with at least one of a shaft, pin or cam type element being eccentrically mounted with respect to a rotational axis. The first motion transmitting element and the further transmitting element are mounted so as to produce a cyclic linear motion at a relative angle to a center axis of rotation of the drive shaft.

The at least one first motion transmitting element is formed by at least two wheel, disc or cylindrical elements located opposite one another. Each of the at least two elements are provided with at least one eccentric element on the outside, and with the eccentric elements being connected with a supporting element rotatable around the at least one motion transmitting element and displaceably mounted in the cyclic linear direction. The supporting element is effectively linked with at least a portion of the cleaning elements to produce a reciprocating motion and at least a portion of at least one of the cleaning elements.

According to the present invention, a further motion transmitting element is provided between the drive unit and the at least one first motion transmitting element by means of which additional motion transmitting element drive is transmitted from the drive shaft to the first motion transmitting element about a rotational axis of the further motion transmitting element. The rotational axis is at an angle to the axis of rotation of the drive unit, and the axis of rotation of the at least one first motion transmission device is at an angle relative to the rotational axis of the further motion transmission element.

According to the present invention, the tooth cleaning elements are mounted in such a fashion that they are free to pivot around a pivot axis and are provided in an area of the pivot axis with roller or gear-type rotational elements for effecting linking of the tooth cleaning elements by, for example, friction, with the roller or gear type elements being rotatable around the pivot axis against a complimentary wall resting against or engaging the wall during the performance of the reciprocating motion of the tooth cleaning elements to that cyclic linear motion of the tooth cleaning elements is effected.

The rotor or gear type elements of the two cleaning devices of the present invention are connected by friction with the pivot axis and/or with at least a portion of at least one of the cleaning elements in such a manner that the cleaning element or elements are driven into one pivot position during rotation in one direction and are driven into the other position during rotation in the other direction.

The tooth cleaning device of the present invention with a drive unit to support the tooth cleaning includes a tensioning or click-spring type means for effectively linking the cleaning elements and positioning the cleaning elements in two pivot positions. The cleaning elements located opposite to one another act in opposite directions and are pivotably mounted on the pivot axis to pivot from one pivot position to the other and vice versa and also at least one reference system is provided to tension, relax or re-tension the tensioning or click-spring-type means during motion of the pivot axis by a reciprocating motion toward and/or away from the reference system or systems, with the tooth cleaning elements being pivotable inward and outward relative to the cleaning head or disposed in one pivot position or the other.

In accordance with the tooth cleaning device of the present invention, a drive element is provided to create an additional cyclic linear motion as well as a pivot element connected lever wise with at least a portion of the cleaning elements. The pivot element is operable by an additional cyclic linear motion in order to pivot the cleaning elements into one position and spring means are provided by which the cleaning elements are driveable into another pivot position with a pretensioning.

In accordance with the present invention, the tooth cleaning device includes a drive device which is identical to a drive unit and a motion transmitting element is effectively connected with at least two eccentric elements to produce both cyclic and linear motions.

The tooth cleaning element of the present invention has at least one rubber cushioned section in order to be able to adapt optimally to different contours of a tooth.

According to the present invention, in the tooth cleaning device, cleaning elements are also provided which act independently of the drive, preferably, in the central and/or peripheral areas of the cleaning head in order to produce a cleaning action especially in the interdental space.

An important feature of constructing the various tooth-cleaning devices, motion transmission means, spring means, rotational elements, etc. is that the reciprocating motion and the cyclic linear motion of the cleaning elements are superimposed on one another or synchronized in such fashion that when the teeth are cleaned, the cleaning elements are pivoted away during the reciprocating motion in the direction of the teeth, and thus away from the latter, and are pivoted toward the teeth in the vicinity of the roots of the teeth or gums, in order then, during the reciprocating motion from the root of the tooth toward the crown, to exert a certain pressure on the teeth in order to clean them. As soon as the reciprocating motion toward the crown has ended, the cleaning elements are pivoted away from the teeth once more in order to be in the swung-away state during the reciprocating motion that then takes place toward the tooth.

BRIEF DESCRIPTION OF THE DRAWINGS

The invention will now be described in greater detail with examples and with reference to the attached figures.

FIG. 2 is a schematic section through another drive according to the invention for effecting the reciprocating motion of the cleaning elements;

FIG. 3 is a section through a drive according to the invention for effecting the reciprocating and cyclic linear motion of a cleaning element;

DETAILED DESCRIPTION

Figure 1A:
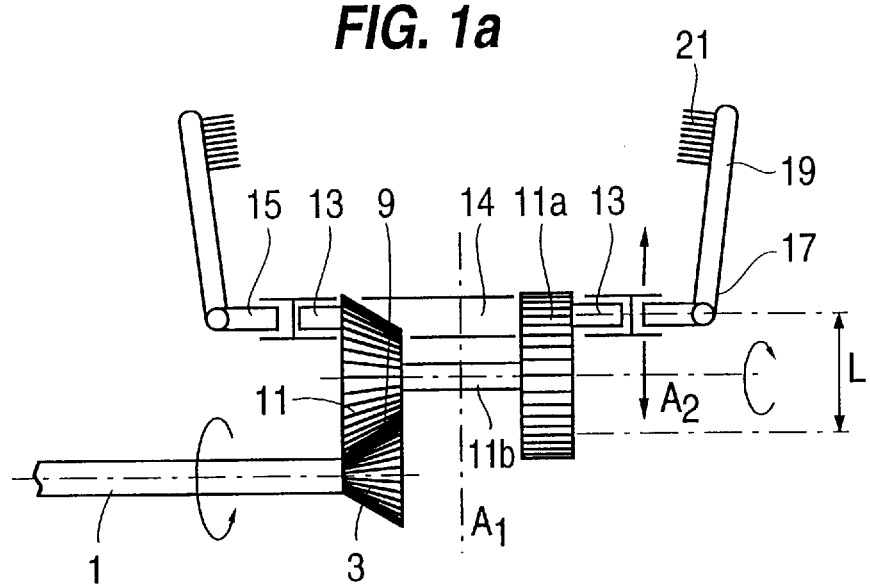
FIG. 1a and FIG. 1b show, schematically in section and in a top view, a drive according to the invention for effecting the reciprocating motion of the cleaning elements.
Figure 1B:
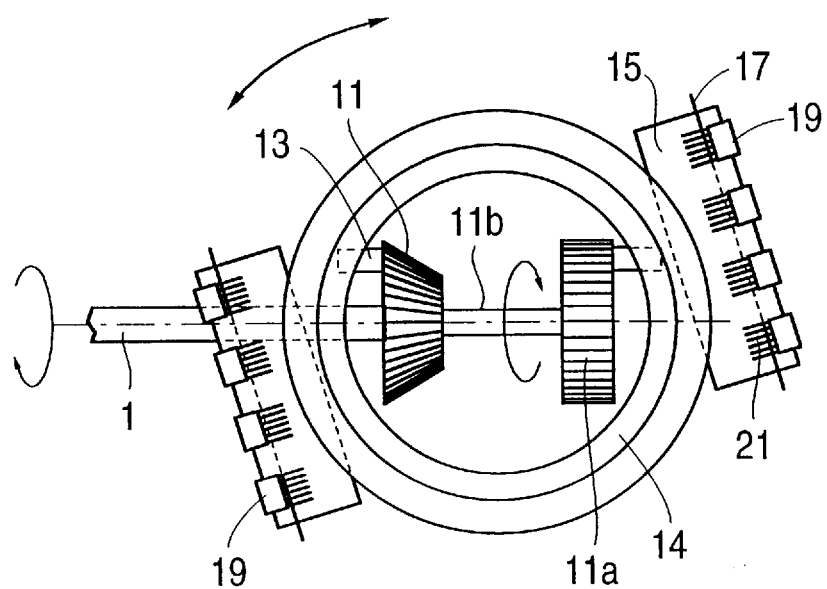

Referring now to the drawings wherein like reference numerals are used throughout the various views to designate like parts and, more particularly, to FIGS. 1a and 1b, a drive according to the invention for a brush head in a cleaning head of an electric toothbrush includes a drive shaft 1 with a bevel gear 11 located in the cleaning head, being driven through a bevel or angle gear 3, for example, by a rechargeable electric motor. This bevel gear 11 has on its periphery a conical toothing 9 meshing with bevel or angle gear 3. This bevel gear 11 rotates around a second axis $A_2$ located essentially parallel to, or at a slightly diagonal angle to, the rotational axis of drive shaft 1. A second gear 11a is rigidly connected with this bevel gear 11, for example by a centrally located rigid drive axis 11b.

On the exterior, the two gears 11 and 11a are each provided with a cam 13, located peripherally and eccentrically, said cam rotating along essentially the circumference of each of the two gears 11 and 11a and around axis $A_2$.

The rotational motion of this cam or pin 13 produces a down cyclic linear motion up and down as shown in the section in Figure 1a, with a carrier part 14 connected with this cam 13 executing an up and down stroke. This carrier part 14 in turn is linked through a connection or mount 15 with cleaning elements, such as brush heads 19, mounted laterally with respect to support part 14 and opposite one another, said brush heads being provided with corresponding bristles 21. These brush heads 19 are also pivotably mounted around an axis 17 on connection or mount 15.

When drive shaft 1 rotates, the two gears 11 and 11a are driven and, through the respective cams and pins 13 located endwise, support part 14 and brush head 19 connected therewith execute a reciprocating motion toward and away from the tooth to be cleaned, with L being the length of the stroke. Since bristles 19 are mounted pivotably movably around axis 17, they can adapt to the outer contour of a tooth. In addition, it follows from the design either that support part 14 is mounted freely rotatably mounted around the two gears 11 or 11a, or connection or mount 15 is mounted freely rotatably around support part 14 therein. This ensures that the brush heads mounted in the cleaning head are likewise freely rotatably movable around an axis $A_1$ and can always adjust to the position of the tooth in this manner, without the user of the toothbrush having to perform corresponding corrective motions with the handle.

In FIG. 2, again in cross section and in schematic form, another drive according to the invention for toothbrushes is shown in the cleaning head of an electric toothbrush. Once again, through drive shaft 1, a conical gear 7 disposed centrally in the cleaning head is driven, with the conical gear being provided with a conical toothing 5 at its periphery, and with the toothing meshing with bevel or angle tooth gear 3. This bevel gear 7 rotates around a first axis $A_1$ that is located essentially at right angles or diagonally with respect to the rotational axis of drive shaft 1. Above this bevel gear 7, laterally in the peripheral area, two gears 11 are provided opposite one another, said gears in turn being driven through a gear drive 9 by bevel gear 7. On their exteriors, the two gears 11 are each provided with a peripherally mounted cam 13 that rotates along essentially the circumference of each of the two gears 11 or around axis $A_2$.

Because of the arrangement of central gear 7, in the arrangement according to FIG. 2 support part 14 can be eliminated, whereby cams or pins 13 can be connected directly by means of connection or mount 15 with the toothbrush elements. Once again, when the drive shaft turns, a reciprocating motion of brush head 19 takes place toward or away from the tooth to be cleaned.

FIG. 3 is a schematic diagram of a similar drive method in which the reciprocating motion according to FIGS. 1 or 2 is superimposed on a largely constrained pivoting motion of brush heads 19. The same components in FIG. 3 have been given the same reference numerals as in FIGS. 1 and 2.

During the rotation of bevel gear 7 and during rotation of gear 11 connected therewith, cam 13 moves along the periphery of the gear, thus producing an up and down motion to generate the reciprocating motion of brush head 19. In the vicinity of pivot axis 17, a gear 23 is disposed on the connection or mount 15 that has a toothing 25 on its outer circumference. This toothing 25 meshes with a matching toothing 27 of a wall 29 located adjacent to brush head 19, for example it is connected permanently with a housing 2 located beneath. During the up and down motion of cam 13 or connection 15, freewheeling gear 23, whose rotational axis is connected with the rotational axis 17 of brush head 19, moves along toothing 27 of wall 29. While gear 23 laterally abuts brush head 19, during rotation of gear 23 brush head 19, because of friction between the gear and the brush head, performs a cyclic linear motion, with brush head 19 pivoting inward during the downward stroke and outward during the upward stroke.

Since gear 23 is connected with brush head 19 laterally by friction alone, assurance is provided that the brush head is tilted forward or backward only up to the maximum pivot positions provided. Especially during the cleaning of the teeth, therefore, the brush is pivoted only as far as the tooth and pressed against the tooth with a certain pressure. Of course it is also possible to link the gear by frictional adhesion with rotational axis 17, but in this case brush heads 19 are rigidly connected with the rotational axis. In addition, it is also possible, instead of a gear connection between "gear" 23 and the wall, to provide only a roughened surface, with gear 23 being moved by the prevailing friction.

Figure 4A:
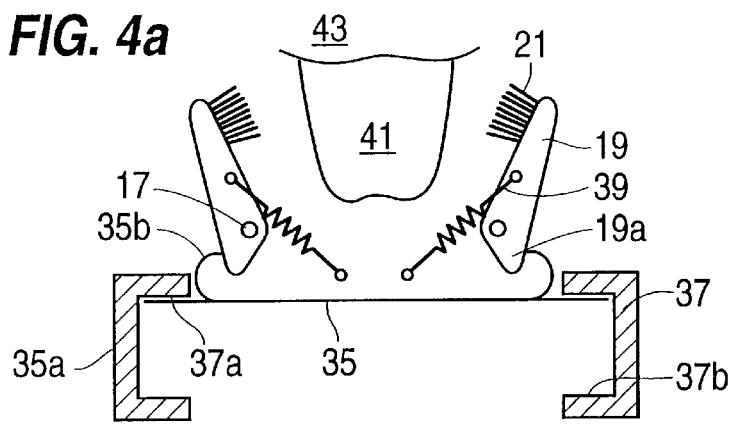
FIGS. 4a to 4c show schematically another embodiment for effecting the cyclic linear motion of the cleaning elements toward the teeth and away from the latter, using tensioning and/or click-spring means.
Figure 4B:
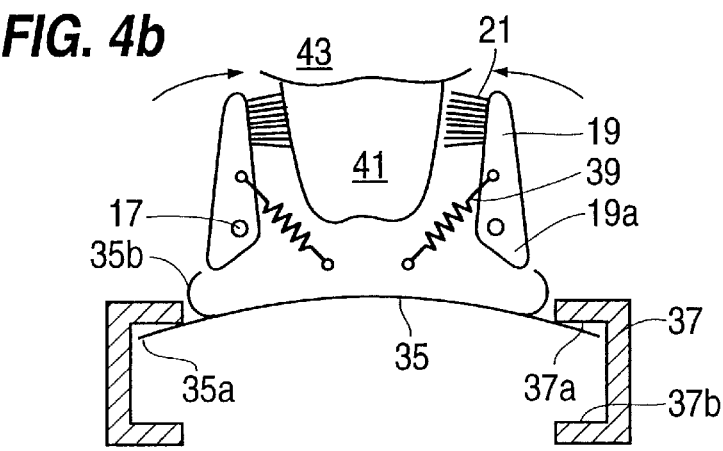
Figure 4C:
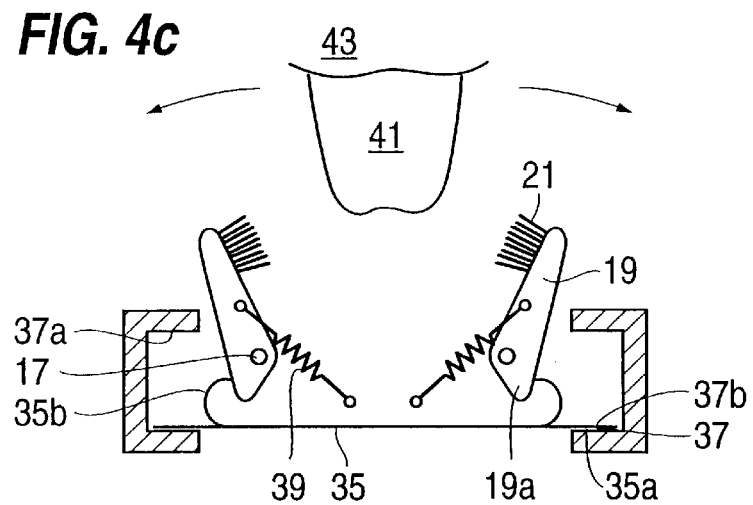

FIGS. 4*a*, 4*b*, and 4*c* each show another possibility of superimposing a pivoting motion on the reciprocating motion of brush heads 19. This is accomplished according to the arrangement shown in FIGS. 4*a* to 4*c* by means of two spring arrangements 35 and 39, with brush heads 19, located opposite one another and acting in opposite directions, each being pretensioned in the direction of the tooth by a spring 39. In opposition to this pretensioning, brush heads 19 are each held in an outwardly pivoted position at their lower ends against a projection 19*a* by an inwardly bent segment 35*b* of a tension or click-spring 35.

During the upward stroke of cleaning elements 19, tensioning or click-springs 35 are each connected with a segment 35*a*, projecting straight endwise, at the lower edge 37*a* of a guide element 37, whereby, as shown in FIG. 4*b*, each of the two inwardly bent segments 35*b* is bent away and downward, so that the two endwise segments 19*a* of brush heads 19 are released. As a result of pretensioning in the direction of the tooth, the two brush heads 19 are tilted inward, so that they abut the contour of tooth 41. This inward tilting motion must then take place when the brush heads are in the "extended" or raised state, i.e. close to gum 43. Then the cleaning of tooth 41 proceeds as brush heads 19 are pulled backward, with bristles 21 being moved away from the gum in the direction of the crown along the surface of the tooth. As soon as brush heads 19 have reached the crown and the brushes are in the "retracted" or lowered state, the two endwise sections 35*a* abut the lower resistant surfaces 37*b* of the two lateral guides 37, whereupon the click or tension springs 35 are retensioned downward, so that the two inwardly bent sections 35*b* again engage the two sections 19*a* and tilt brush heads 19 outward.

Thus, the movement of the brush heads from the crown of the tooth toward the gum takes place in the state in which the heads are tilted apart, for example, bristles 21 touch the tooth slightly if at all, which is desirable.

It has been shown to be advantageous in dental hygiene for the motion of the bristles when cleaning the teeth preferably always to be directed away from the gums and toward the crown, and not in the opposite direction.

Figure 5A:
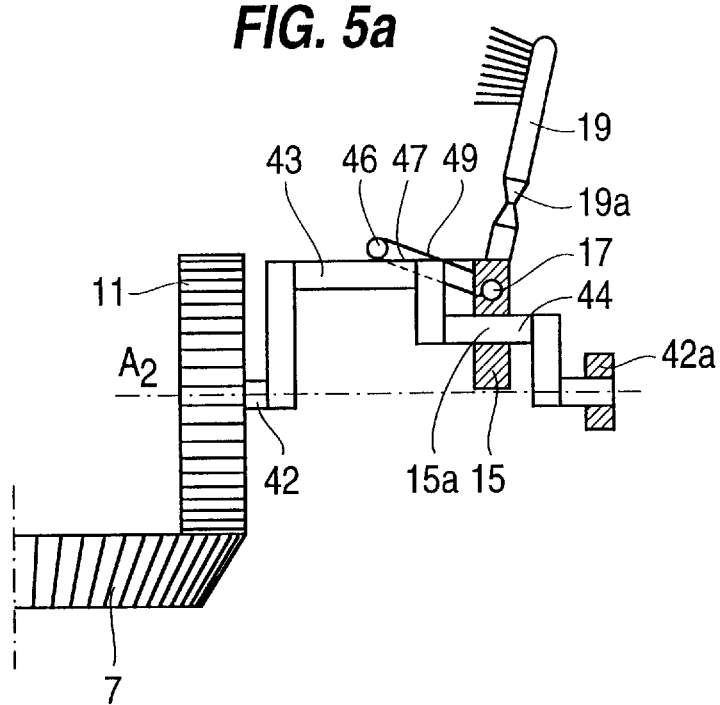
FIGS. 5a and 5b show schematically and in section, another embodiment of a drive according to the invention, especially for synchronous and superimposed effecting of the reciprocating and cyclic linear motions of the cleaning elements.
Figure 5B:
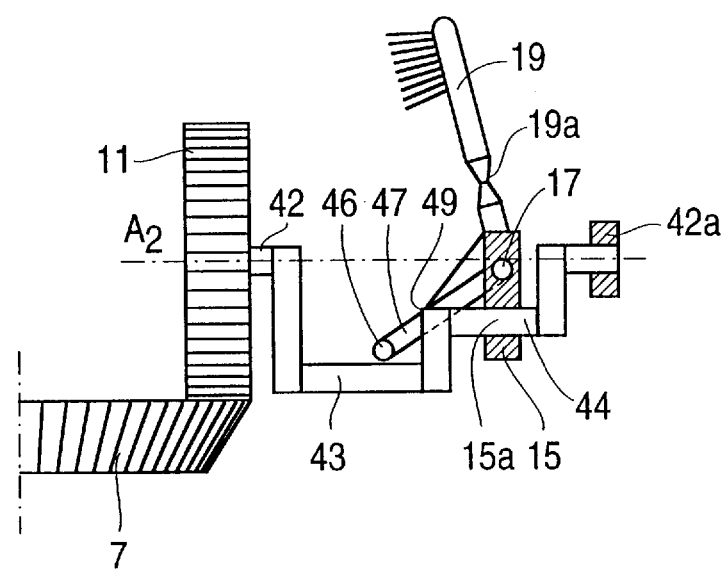

FIGS. 5*a* and 5*b* show another drive variation for the reciprocating motion to be superimposed on a pivoting motion of the brush heads. Once again the drive of a gear 11 is provided by a bevel gear 7, whereby however the drive of course could also be provided directly by bevel gear 3, as shown for example in FIG. 1. Contrary to the diagrams in FIGS. 1 to 3, no peripheral cam 13 is provided on gear 1. Instead, base 15 of brush head 19 is connected with the central rotational axis of gear 11 by an eccentric shaft 42, which has differently eccentric segments. Immediately adjacent to the central rotational axis of gear 11, shaft 42 has a highly eccentric or offset section 43, which a section 44 abuts, with a reduced deflection or eccentricity relative to rotational axis $A_2$ of gear 11. Finally, shaft 42 is held endwise in a bearing 42*a*.

This outer section 44 of the double eccentric connecting shaft extends for example, through a recess a in base 15, on which brush head 19, pivotally movable around axis 17, is mounted. The foot of brush head 19 is also connected by a connecting rod 47 with a tilt lever 46 running parallel to gear 11, said lever having a length much shorter than the lateral deflection of segment 43 in the direction of this tilt lever or this tilt rod 46. Finally, a tensioning spring 49 is also provided to pretension tilt rod 46 and brush head 19 connected therewith, downward and inward.

When bevel gear 7 is rotated by the drive shaft, at the same time double eccentric rod 42 is rotated around axis $A_2$ by the motor transmitter or gear 11, whereby firstly, by the segment 44 located eccentrically relative to gear 11, the reciprocating motion of base part 15 and brush heads 19 connected therewith is executed. The brush heads are pretensioned inward by tensioning springs 49. During the rotation of segment 43, the latter engages rod 46 from below during its outward motion and drives it upward. By the connecting rod 47, brush heads 19 are pivoted simultaneously on the axis 17 in the direction of the arrow shown in FIG. 5*a* and outward toward the tooth to be cleaned.

After performing the stroke in the direction away from the tooth cleaning head and toward the tooth, segment 43 again releases rod 46 because of its lateral deflection, whereupon the latter tilts downward because of the tensioning force of pretensioning spring 49, whereupon brush heads 19 are tilted inward simultaneously in the direction of the tooth. Therefore, the situation is again created in which brush heads 19 are tilted outward during the reciprocating motion from the lowered state into the raised state, whereupon brushes 21 contact the tooth as well as the gums little if at all. As soon as the brush heads are in the raised state, they are tilted inward in order to perform a cleaning motion with brushes 21 from the gums toward the crown of the tooth. By providing a flexible or elastic zone 19a on brush heads 19 the brush head can also be made to adjust individually to the external contour of a tooth.

In FIGS. 6 to 13 which follow, the drive possibilities shown schematically in FIGS. 1 to 5 are shown with regard to specifically designed cleaning heads of so-called electric tooth-cleaning devices.

Figure 6:
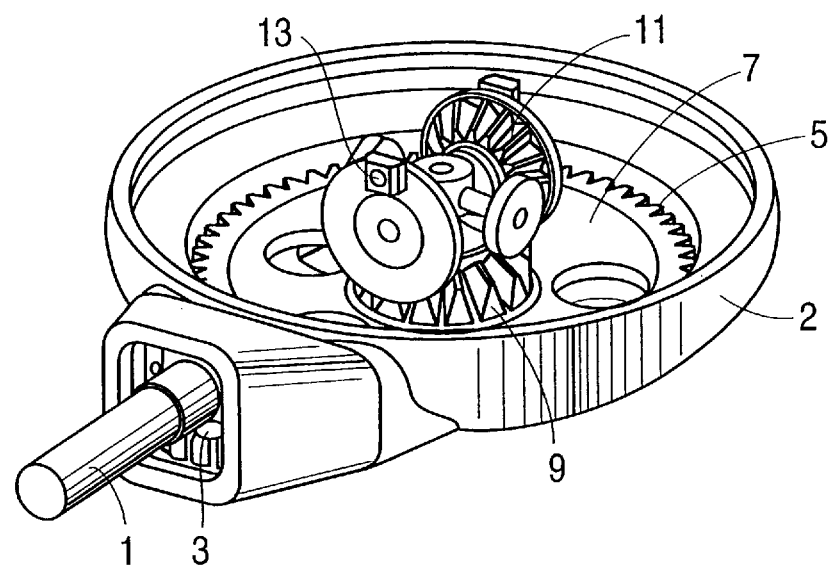
FIGS. 6 and 7 show a cleaning head schematically and in cross section, comprising the drive according to the invention analogous to FIG. 3.
Figure 7:
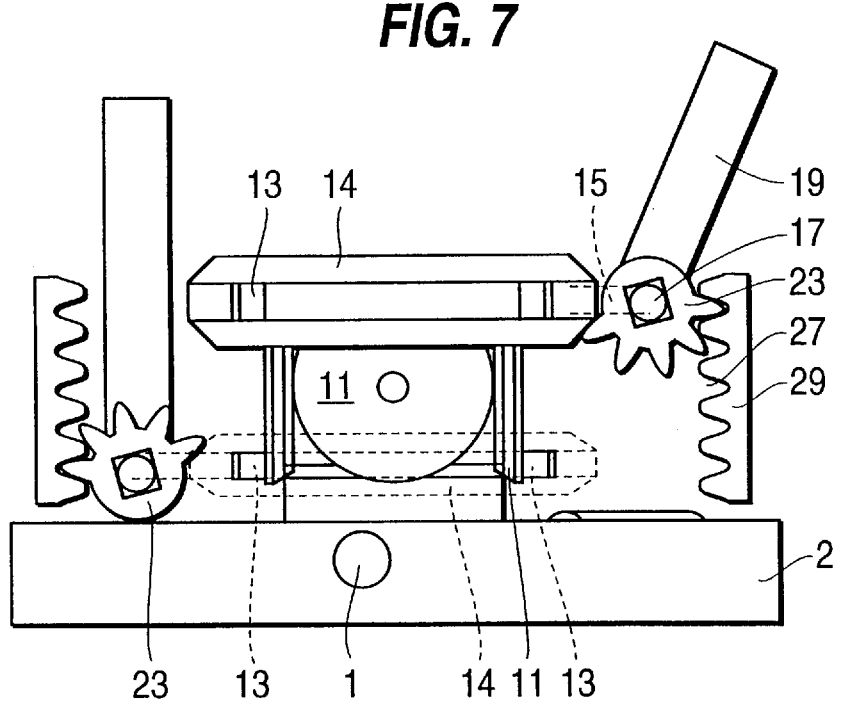

FIGS. 6 and 7 show the design of a cleaning head comprising a drive mechanism similar to that in FIG. 3. Here FIG. 6 shows the base part 2 of the cleaning head in which the drive is effected for example by a handle with an electric motor through a drive shaft 1. Through bevel gear 3 mounted endwise on drive shaft 1, a corresponding bevel gear 7 is driven that rotates the first axis that runs centrally in the cleaning head, essentially perpendicularly to the drive shaft. The drive of bevel gear 7 however can also be provided peripherally, for example, by the drive shaft 1 through a worm drive.

Through a centrally located toothing 9, the drive is transmitted to motion transmitter or gears 11, each of which has eccentrically disposed cams 13 in its outer surface in the peripheral area. The brush heads are not shown in FIG. 6, in order better to show the transmission of the drive to the motion transmitter or gears 11.

FIG. 7 shows a section through the cleaning head, with the engagement of drive shaft 1 in base part 2 being shown schematically. Once again the two gears 11 are driven by bevel gear 7 (not visible) through gear drive 9. The two cams mounted endwise on gears 11 mesh with a support part 14 that is essentially circular and surrounds the two gears, and is freely movable and performs the reciprocating motion together with cams 13 engaging therein. In FIG. 7, a raised position of this carrier part 14 is shown by the solid lines and a corresponding lowered position is shown by the dashed lines. Laterally, this support part 14 is connected by a connection or a base part 15 with rotational axes 17 of brush heads 19, which are simultaneously the rotational axes of gears 23. These gears 23 mesh externally with corresponding notches 27 of a wall 29, said wall for example being connected rotationally movably with base part 2. Because of the raised position of a gear 23, brush head 19 is mounted pivoted outward.

By lowering support part 14 into the position indicated by the dashed lines, the other gear 23 rotates along thread 27 around axis 17, so that brush head 19 connected therewith is moved into the position shown at the left, pivoted inward. Of course, both the brush heads located opposite one another can be pivoted simultaneously inward or outward; the drawing in FIG. 7 was chosen to show both positions simultaneously in one figure.

During motion of gear 23 downward, the pivoting motion of the brush head inward takes place immediately after rotation of the gear, and over the remaining distance during the reciprocating motion the brush head and the gear rub against one another, since the connection from the gear to the brush head is by friction alone. The same process is repeated during the upward motion of the gear, whereby immediately after the beginning of the reciprocating motion, the brush head is tilted outward and then rubs on the gear. It is then possible for the gear to be connected firmly with the pivot axis, but brush heads 19 are mounted freely on the rotational axis and adhere laterally to gears 23 by friction. Alternatively, the brush heads can be permanently connected with the rotational axis and gears 23 can be connected with this pivot axis by friction.

Of course it is also possible to provide instead of a gear only a peripheral frictional surface on "gear" 23, which rolls on a corresponding frictional surface on side wall 29 It is important that as a result of the rolling of wheel 23, brush head 19 connected therewith is pivoted inward or outward.

Figure 8:
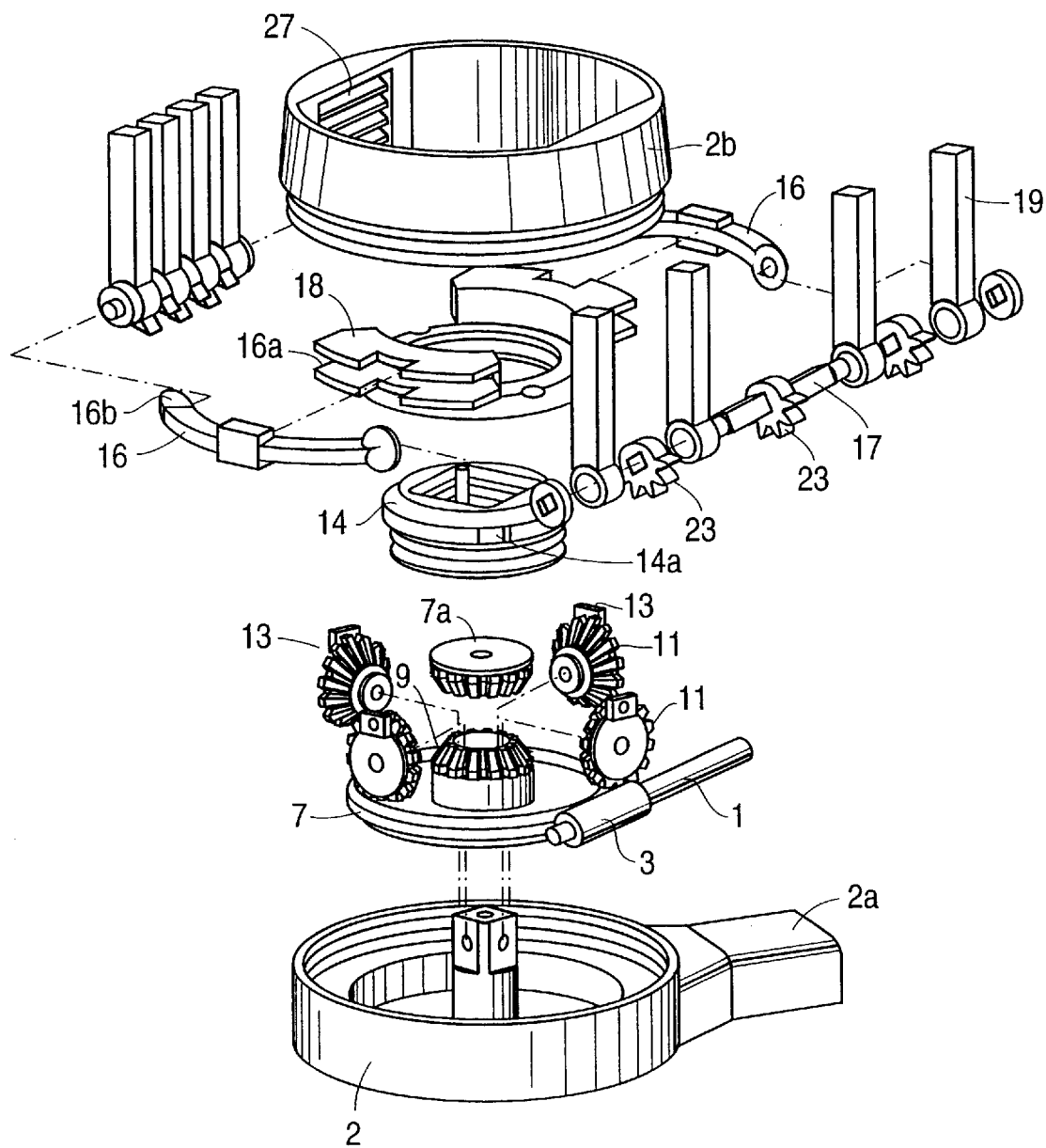
FIG. 8 is a cleaning head in an exploded view and in a perspective view, comprising a drive similar to that shown in FIGS. 6 and 7.

FIG. 8 shows in an exploded view, a cleaning head similar to FIGS. 6 and 7 of an electric toothbrush, comprising base part 2 with a holding part 2a and a wall 2b rotationally movably connected with base part 2. Once again the drive is provided by drive shaft 1 through endwise worm gear 3 on a gear 7 located centrally in base part 2. From this gear 7, the drive is transmitted through a central gear 9 to four symmetrically arranged bevel gears 11, which are covered by another bevel gear 7a to ensure synchronous operation. The four endwise cams 13 each engage a recess 14a of support part 14 that is freely movable in the stroke direction, in order to confer a cyclic linear motion on this support part 14. A holding part 18 with lateral notches 16a is disposed so that it rests on this support part 14, into which lateral notches 16a holders 16 have been inserted, each holding, with endwise contact surfaces 16b applied with pressure, the two rotary bearings 17, surrounding brush head 19 and gears 23. Of course, gears 11, support part 14, holding part 18, holders 16, and gears and brush heads 19 can all be located inside rotationally movable wall 2b.

Figure 9:
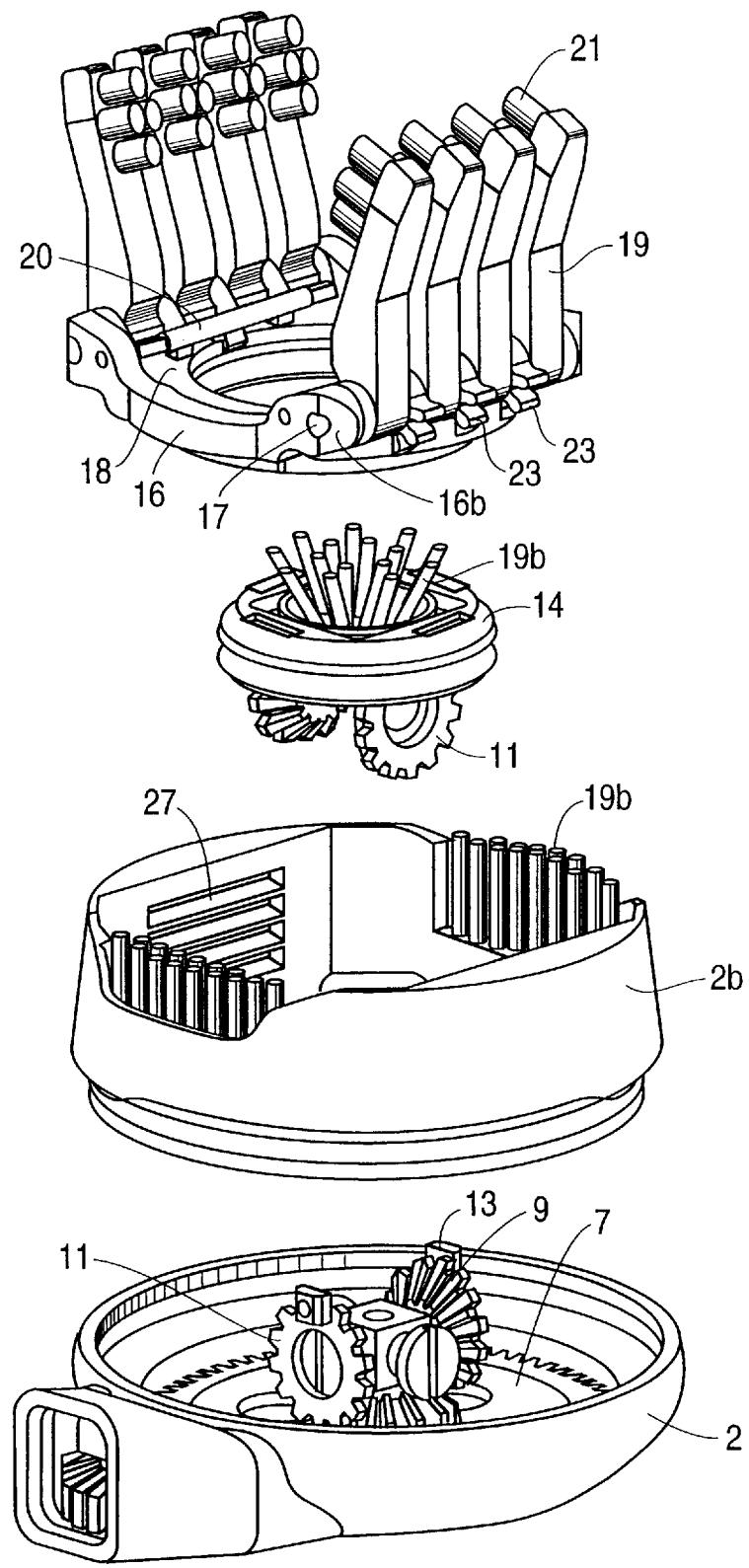
FIG. 9 is another embodiment of a cleaning head comprising the same drive mechanism as in FIGS. 6 to 8.

FIG. 9 shows the same tooth-cleaning head according to FIG. 8 in a partially assembled state, whereby in particular brush heads 19 located opposite one another, gears 23 with holding part 18, and holders 16 are shown permanently connected or permanently pressed together. In order to ensure friction between gears 23 and brush heads 19 and possibly to adjust them after a certain amount of wear, two retaining rods 20 are also provided to hold together permanently the two lateral holders with holding surfaces 16b.

In contrast to FIG. 8, the cleaning head shown in FIG. 9 has only two central gears 11 opposite one another for transmitting the drive from gear 7 to support part 14. On the other hand, on support part 14, shown schematically, additional cleaning elements or brushes 19b are provided, permanently attached to support part 14, for example for cleaning the interdental space or the flat parts of the teeth located on the crown.

Figure 10A:
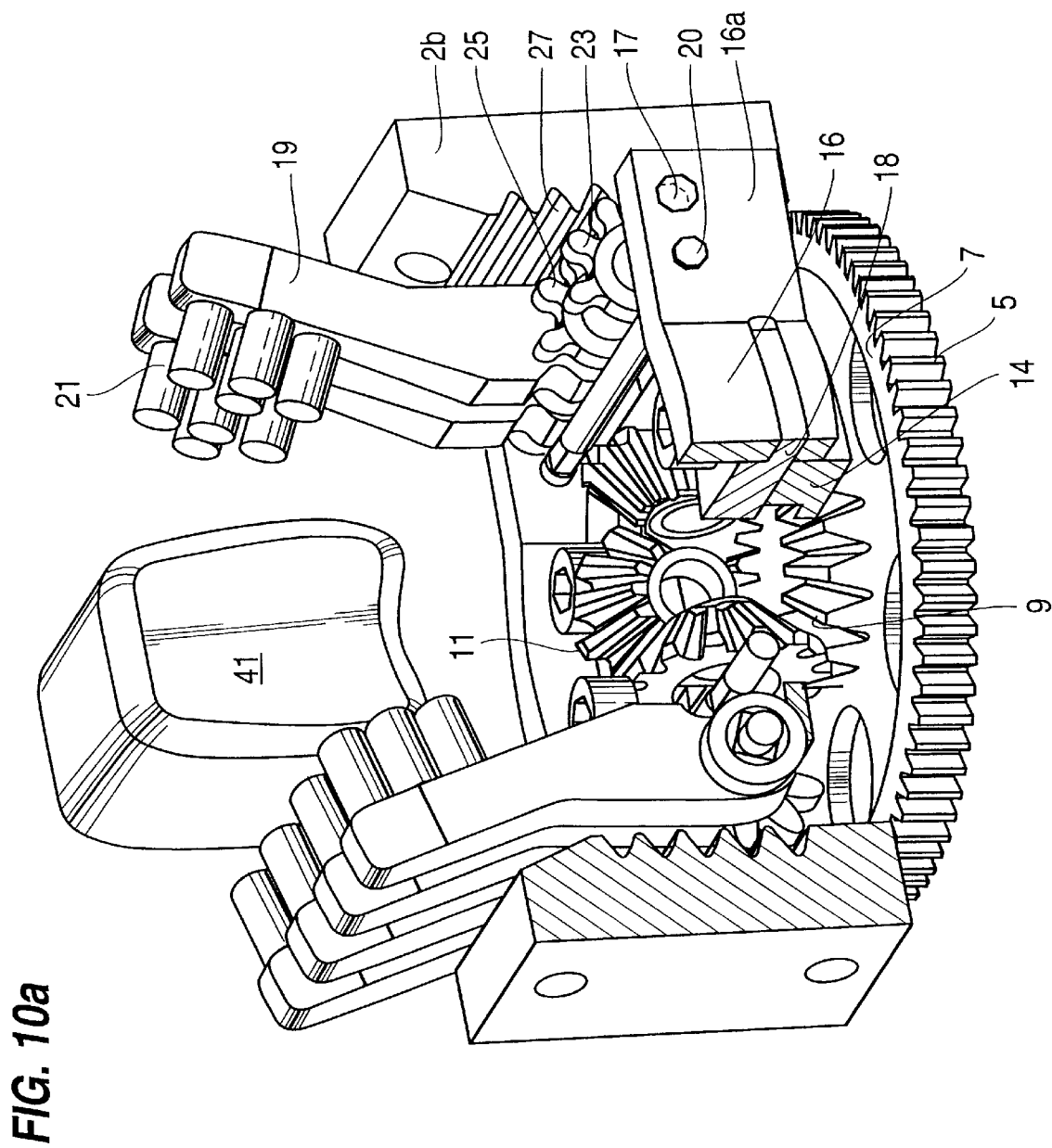
FIGS. 10a to 10d show the function of the cleaning heads or drive according to FIGS. 8 and 9.

FIGS. 10a to 10d show the function of a tooth-cleaning head according to FIGS. 8 and 9. In FIG. 10a, support part 14, holder part 18, and lateral holders 16 and brush heads 19 connected with them are shown in the lowered state, for example, in a position in which they are not in contact with a tooth 41 to be cleaned.

Figure 10B:
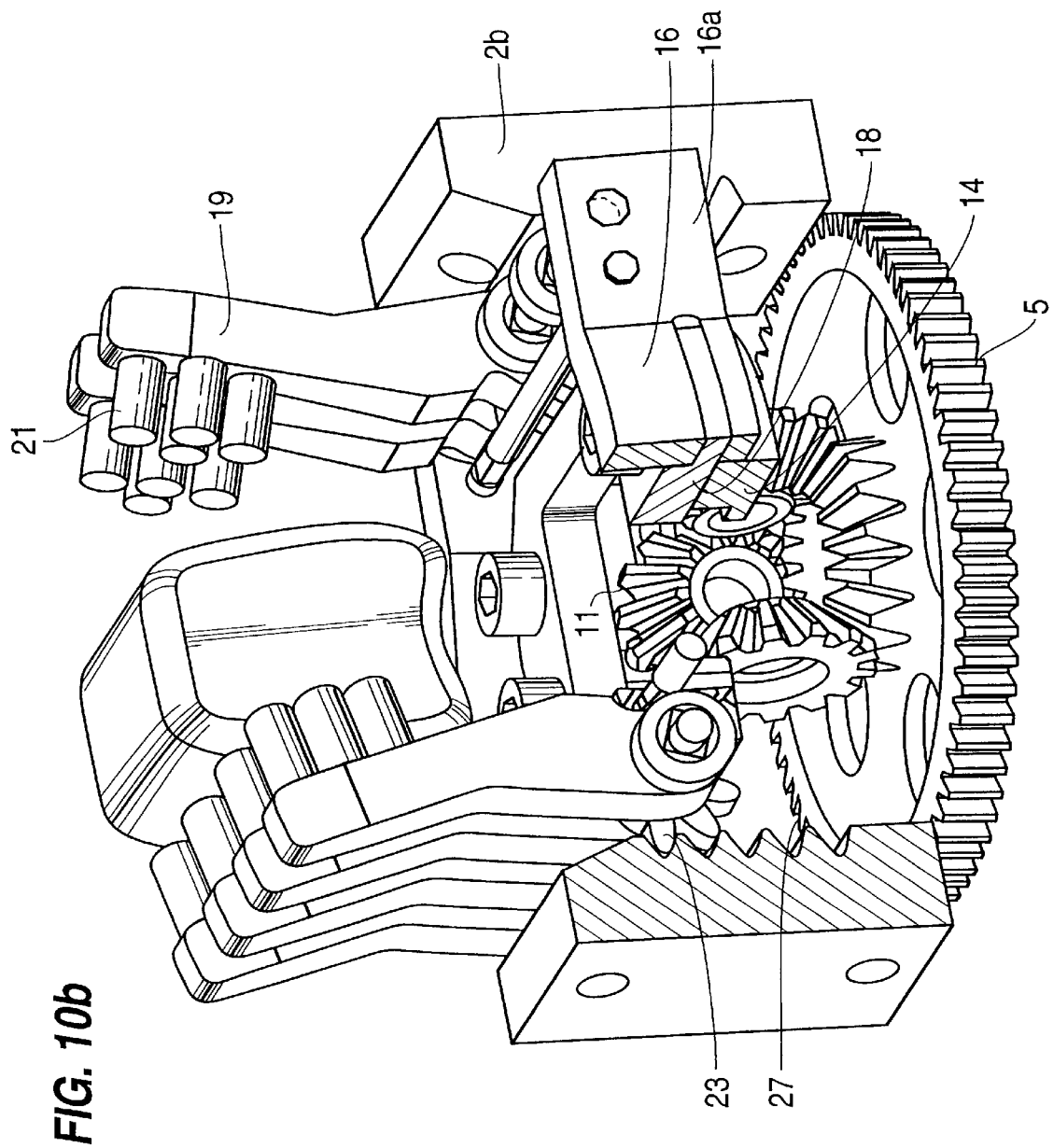

In FIG. 10b, the entire cleaning system is shown, whereby lateral holders 16 and brush head 19 are moved upward by means of cams 13, not shown, support part 14, and holder part 18 connected therewith. At the same time, as the result of engagement in lateral threaded notches 27, gears 13 are rotated outward, whereby immediately at the beginning of the upward stroke, brush heads 19 are immediately tilted outward away from the tooth as a result of lateral friction. As soon as brush heads 19 are in the backwardly tilted state, gears 23 slide laterally on the brush heads, but without tilting them further backward.

Figure 10C:
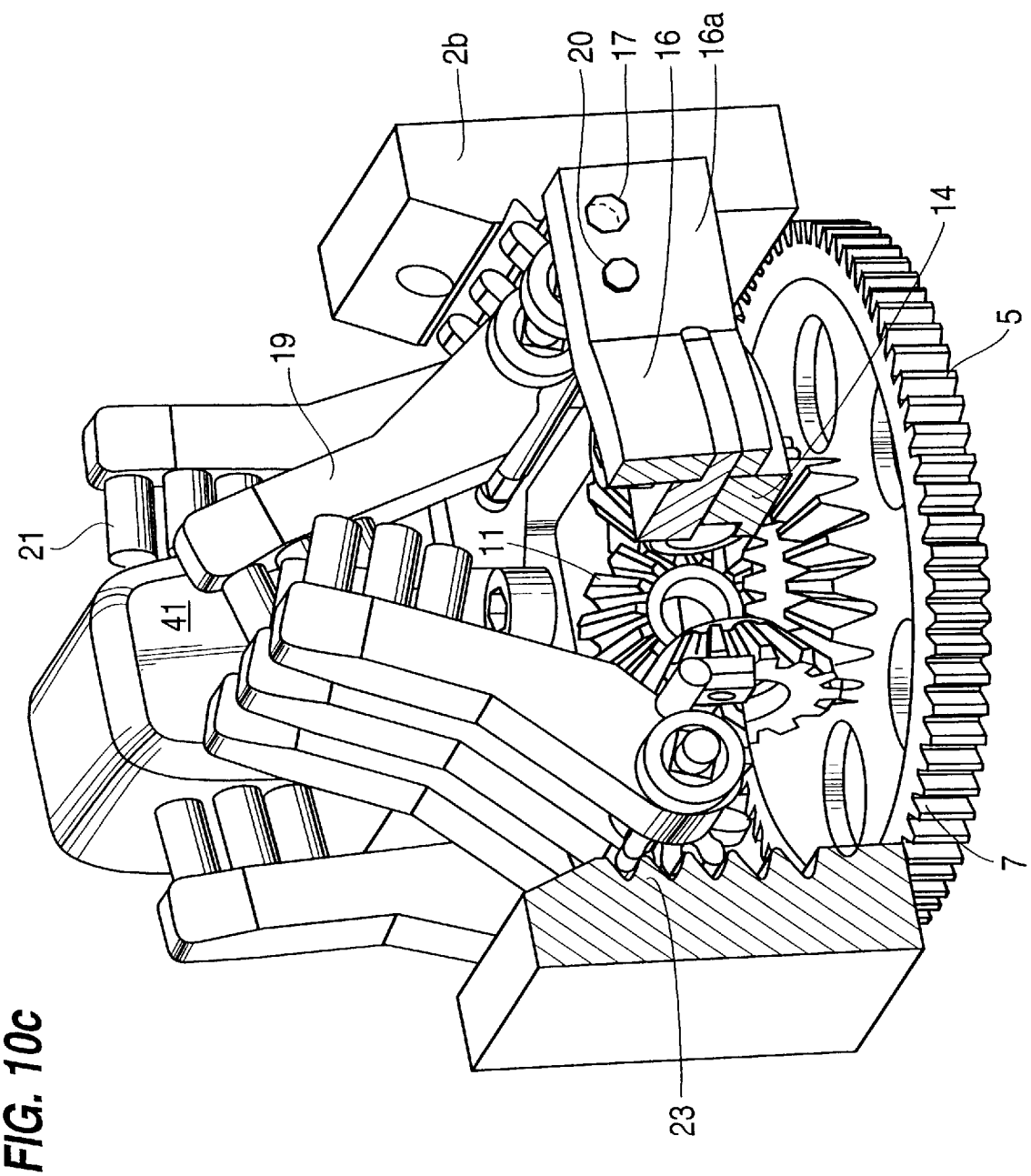

As soon as the upward motion of cams 13 is ended and the corresponding downward cyclic linear motion of cams 13 begins, gears 23 each rotate inward, whereby, as can be seen in FIG. 10c, the brush head are tilted inward against the tooth once again as a result of lateral friction. The downward stroke thus produces a cleaning action on the tooth from the gum toward the crown, which is desirable from the dental technology standpoint.

Figure 10D:
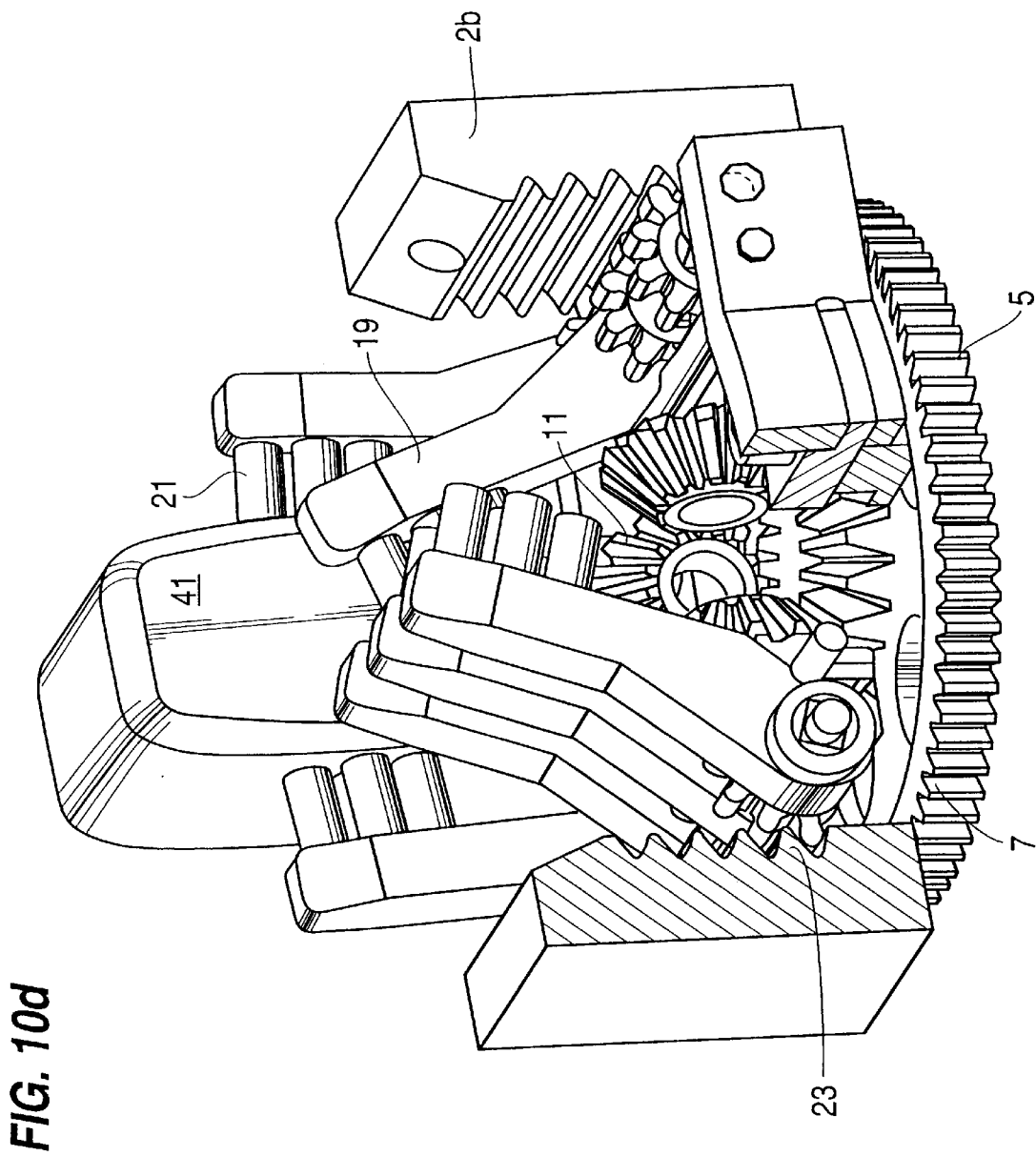

Finally, the cleaning arrangement is shown once again in FIG. 10d after a lowering motion has been completed, with the brush heads still in the inwardly pivoted state. Then in FIG. 10d, the brush heads, as shown in FIG. 10a, are tilted outward again as a result of their upward motion.

Figure 11:
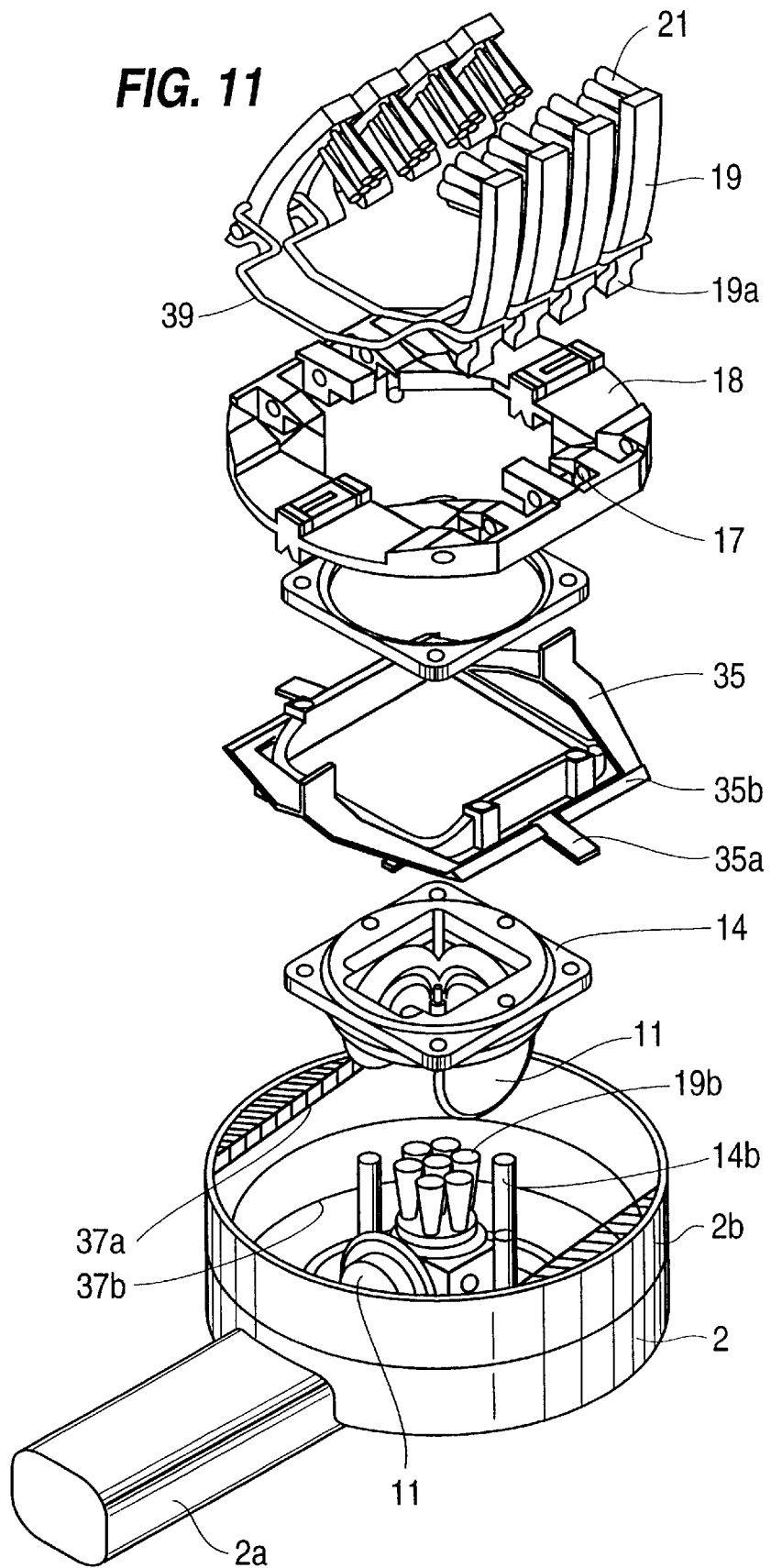
FIG. 11 shows another cleaning head in perspective and in an exploded view, comprising a drive according to FIGS. 4a to 4c.

In FIG. 11, another cleaning head of an electric toothbrush is shown in an exploded view, whereby four centrally disposed gears 11 are driven once again by a drive shaft (not shown) in base part 2 of the cleaning head, with the gears conferring a cyclic linear reciprocating motion on a centrally disposed part 14. Once again a holding part 18 is disposed on this support part 14, in which two brush head arrangements 19 are located opposite one another on pivot axes 17. These brush heads 19 are pretensioned inward by spring elements 39. An additional tilting or tensioning spring 35, similar to the arrangement according to FIGS. 4a to 4c, is provided between retaining element 18 and support part 14. This tensioning or tilting spring 35 serves to drive each of brush heads 19 outward at their lower segments 19a by parts 35b that are bent endwise. The function of the cleaning head in FIG. 11 will not be described and the reader is referred to FIGS. 4a to 4c.

Tensioning or tilting spring 35 is tensioned upward or downward by means of straight sections 35a projecting endwise, with matching contact surfaces 37a and 37b being provided on upper rotatable wall 2b of the cleaning head.

In addition to the figures described above, FIG. 11 shows more guide elements 14b to ensure reliable cyclic linear travel of support part 14 within the cleaning head. Once again, in the middle of the cleaning head, brush heads 19b are shown permanently attached, e.g. suitably for cleaning the interdental space.

Figure 12:
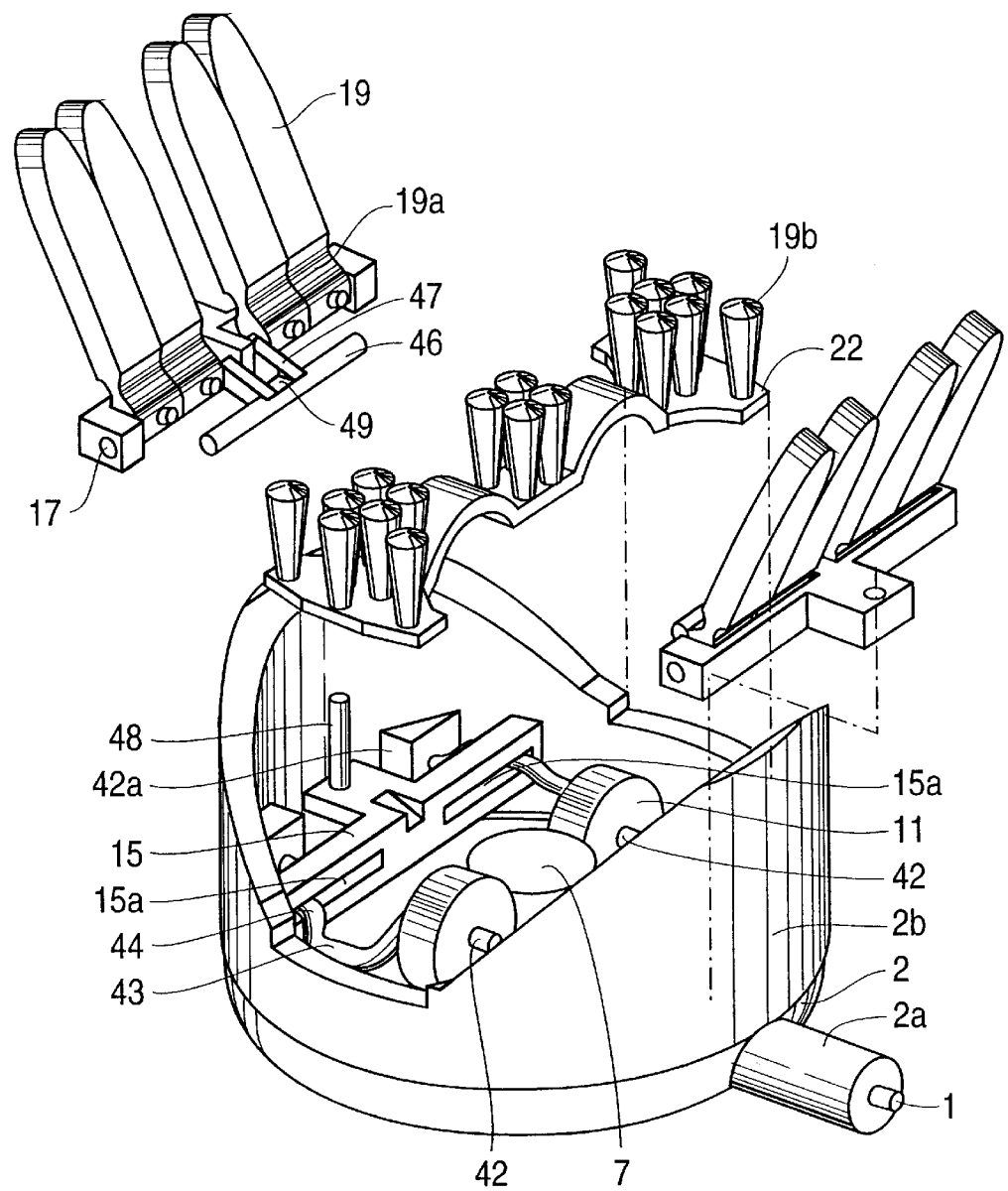
FIG. 12 shows another cleaning head comprising the drive according to FIGS. 5a and 5b.
Figure 13:
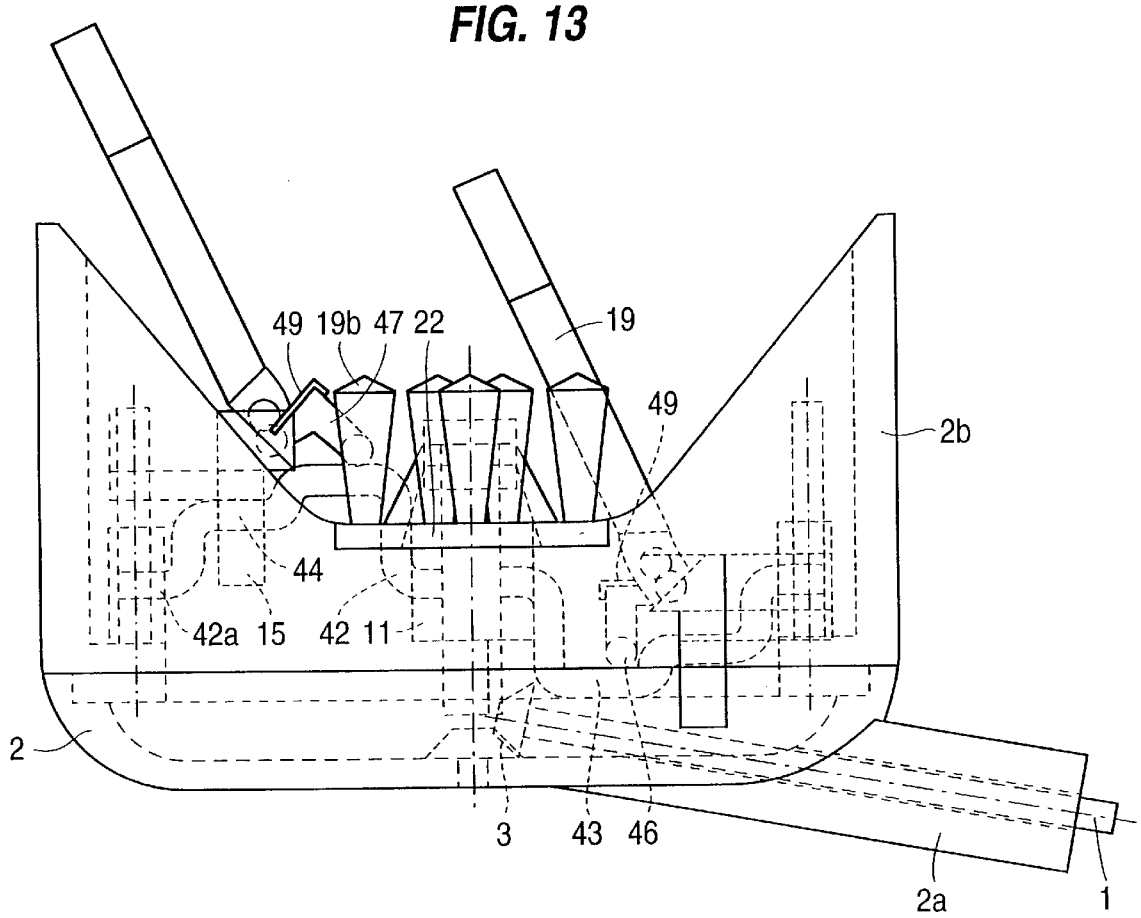
FIG. 13 shows a section of the cleaning head in FIG. 12 to illustrate the function of the drive mechanism according to FIGS. 5a and 5b as well as FIG. 12.

Finally in FIGS. 12 and 13, in a perspective view and in a section, and once again in an exploded view or in an assembled view, another cleaning head is shown that has a drive similar to those in FIGS. 5a and 5b.

Through drive shaft 1, the drive is once again transmitted for example from a handle to centrally disposed gear 7, which for example transmits the drive to the two gears 11 through a worm gear drive. Thus, gear 7 together with one of the two gears 11 forms a so-called worm gear pair. On both sides of the two gears, as shown in FIG. 5, double eccentric rods 42 are provided, connected with gear 11 in the central rotational axis and mounted endwise in bearings 42a. These double eccentric rods comprise firstly a section 43 with a large deflection and a section 44 offset with respect thereto, with a small deflection, whereby the latter section engages recesses 15a of a base support part 15 on which brush heads 19 are mounted. This supporting base part 15 is displaceably mounted in guides 48 in order to execute the reciprocating motion together with brush heads 19. Once again, four brush heads 19 are provided, but bristles 21 have been omitted for the sake of clarity.

Centrally in the brush arrangement comprising the four brushes 19, a tilt lever is provided surrounding a connecting pin 47 and an endwise tilt rod 46, with connecting pin 47 being connected through rotational axis 17 with brushes 19. Lowering tilt rod 46 pivots the brushes inward, while an upward tilting motion pivots the brushes upward. By means of another tensioning spring 49 that is provided, brush heads 19 and the tilt lever, comprising rod 47 and connection 47, are pretensioned inward and downward, so that without any external influence, brushes 19 are mounted tilted inward. Advantageously, the brushes can then adapt to individual tooth shapes, and so they each comprise in the vicinity of their foot points flexible parts 19a made, for example, of a rubber-elastic or elastomer material, for example, Desmopan made by Beyer. However, any elastomeric polymer materials can be used for the purpose which meet the corresponding requirements for use in dental hygiene.

Another mounting plate 22 is provided centrally and overlapping gears 7 and 11, on which plate brushes 19d suitable for cleaning the crowns of the teeth are mounted centrally, which is especially advantageous for the teeth disposed endwise in the jaw.

During operation of a cleaning head according to FIGS. 12 and 13, the four eccentric rods 42 each rotate around the central rotational axis of the two gears 11, whereby sections 43 engage tilt lever 46 from below and drive the latter upward. Consequently, brush heads 19 are tilted outward, so that the brushes are not in contact with the teeth during the reciprocating motion in the direction of the teeth. After the upward stroke has been performed, produced by sections 44 of eccentric rods 42, sections 43, since they are mounted displaced or angled laterally with respect to sections 44, are deflected outward, whereupon rod 46 is released and tilts downward. Immediately, as a result of the spring force of tensioning springs 49, brush heads 19 are tilted inward, whereupon the brushes clean the teeth during the downward stroke.

The drive mechanisms shown in FIGS. 1 to 13 and correspondingly structured cleaning heads of course merely constitute examples of what could be changed in any way or manner, modified, or supplemented. It makes no difference whether the transmission of force from the drive shaft takes place with a bevel gear drive, by a helical gear pair, or by a worm gear drive; the important thing as that firstly a motion transmitting element is driven by the drive shaft to produce a cyclic linear motion. By this cyclic linear motion, firstly a reciprocating motion of the cleaning elements is produced and secondly, preferably simultaneously, a cyclic linear motion or a tilting motion of these cleaning elements is effected.

However, the cyclic linear motion or the tilting motion of the cleaning elements can also be produced by an independent drive element, for example a pneumatic or hydraulic drive element.

It is also immaterial of what materials the individual drive elements, shafts, housing, etc. are made. For example the drive shaft is preferably made of metal, while the drive elements disposed in the cleaning head as well as the motion transmitting elements, gears, etc. are made of plastic, which firstly exhibits high abrasion resistance and secondly is resistant to hot water. The important criteria for choosing the structural material, especially a plastic, are mechanical stress and possibly chemicals, or resistance to hot water. Such materials for making cleaning heads of electric toothbrushes are already well known, however, so that optimum materials will not be named at this point.

I claim:

1. A method of driving at least one tooth cleaning element in a tooth cleaning device comprising:

a rotary drive including a rotating shaft;

providing a non-eccentric motion around a first axis in response to rotation of the shaft of the rotary drive rotating around another axis which is not parallel to the first axis;

converting the rotary motion around the first axis into non-eccentric rotary motion about a second axis which is not parallel to the first axis; and converting the rotary motion about the second axis into cyclical linear motion of the at least one tooth cleaning element which cyclical linear motion is essentially parallel to the first axis.

2. A method in accordance with claim further comprising:

rotating the at least one cleaning element during the cyclical linear motion.

3. A method according to claim 2, wherein the step of rotating the at least one cleaning element includes displacing a rotary member along a planar member cooperable with the rotary member.

4. A method according to claim 3, wherein the planar member is parallel to the cyclic linear motion.

5. A method in accordance with claim 1 further comprising:

a pivot axis, connecting a motion transmitter driven by the rotary motion about the second axis, to each of the at least one cleaning element; and the rotary motion about the second axis causes each of the at least one cleaning element to pivot about the pivot axis with pivoting being in one direction upon an upward linear motion of each cleaning element and in an opposite direction upon downward linear motion of each cleaning element.

6. A method according to claim 5, wherein the cyclical simultaneously produces at least one of cyclic linear and reciprocating motion of the pivot axis of the at least one cleaning element and, simultaneously, through rotation of the rotary unit, causes the at least one cleaning element to perform a cyclic linear motion.

7. A method according to claim 1, wherein, the cyclic linear motion produces a reciprocating motion of the at least one tooth-cleaning element relative to teeth to be cleaned.

8. A method according to claim 7, wherein at least two relative motions of the at least one tooth-cleaning element are produced relative to the teeth to be cleaned.

9. A method according to claim 8, wherein the cyclical linear motion is a reciprocating motion and a pivoting motion around a pivot axis of the at least one tooth cleaning element.

10. A tooth cleaning device comprising:

a rotary drive including a rotating shaft;

a first transmission element, coupled to the rotary drive, providing a non-eccentric motion around a first axis in response to rotation of the shaft of the rotary drive rotating around another axis which is not parallel to the first axis;

a second transmission element, coupled to the first transmission element for converting the rotary motion around the first axis into non-eccentric rotary motion about a second axis which is not parallel to the first axis; and a third transmission element, coupled to the second transmission element for converting the rotary motion about the second axis into cyclical linear motion of at least one tooth cleaning element which cyclical linear motion is essentially parallel to the first axis.

11. A tooth cleaning device according to claim 10, further comprising a handle and a head part, said at least one cleaning element is mounted at or in a cleaning head located substantially endwise on said head part, and wherein at least two portions of the at least one cleaning element are mounted opposite one another and act against one another in order to produce at least one cyclical linear motion relative to the cleaning head.

12. A tooth cleaning device according to claim 11, wherein the at least two portions of the at least one cleaning element on the cleaning head, as viewed from a tooth, surround the tooth in a concave manner so that the at least one cleaning element surround the teeth on at least two sides thereof.

13. A tooth cleaning device according to claim 11, wherein the cleaning head is composed of at least two parts, and wherein the at least two parts are movably connected with each other.

14. A tooth cleaning device according to claim 11, wherein the third transmission element is eccentrically mounted with respect to the second rotational axis and is mounted to produce a cyclical linear motion at an angle relative to the another axis of rotation of the drive shaft.

15. A tooth cleaning device according to claim 14, wherein said drive shaft is connected to the first transmission element by one of a worm gear, a bevel gear or an angle gear.

16. A tooth cleaning device according to claim 14, wherein the third transmission element is formed by at least two elements located opposite one another, each of said at least two elements are provided with at least one eccentric element, said eccentric elements being connected with a supporting element rotatable around the second transmission element and displaceably mounted in a cyclic linear direction, and wherein said supporting element is linked to at least one cleaning element to produce a reciprocating cyclical linear motion in at least one cleaning element.

17. A tooth cleaning device according to claim 16, wherein said at least two elements of the at least third transmission element is one of a wheel, disc or cylindrical element.

18. A tooth cleaning device according to claim 14, wherein the at least one tooth cleaning element is mounted to be freely pivotable around a pivot axis and is disposed in an area of a pivot axis of the third transmission element.

* * * * *